United States Patent
Jain et al.

(10) Patent No.: US 9,777,014 B2
(45) Date of Patent: Oct. 3, 2017

(54) TETRAHYDRO-2H-PYRANO[3,2-C] ISOCHROMENE-6-ONES AND ANALOGS FOR THE TREATMENT OF INFLAMMATORY DISORDERS

(71) Applicant: Council of Scientific & Industrial Research, New Dehli (IN)

(72) Inventors: Shreyans Kumar Jain, Jammu (IN); Tabasum Sidiq, Jammu (IN); Samdarshi Meena, Jammu (IN); Anamika Khajuria, Jammu (IN); Ram Asrey Vishwakarma, Jammu (IN); Sandip Bibishan Bharate, Jammu (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 14/891,706

(22) PCT Filed: Nov. 1, 2013

(86) PCT No.: PCT/IN2013/000679
§ 371 (c)(1),
(2) Date: Nov. 17, 2015

(87) PCT Pub. No.: WO2014/188440
PCT Pub. Date: Nov. 27, 2014

(65) Prior Publication Data
US 2016/0122360 A1    May 5, 2016

(30) Foreign Application Priority Data
May 24, 2013    (IN) ............................ 1565/DEL/2013

(51) Int. Cl.
*C07D 493/04*    (2006.01)

(52) U.S. Cl.
CPC ................. *C07D 493/04* (2013.01)

(58) Field of Classification Search
None
See application file for complete search history.

(56) References Cited

PUBLICATIONS

International Search Report for International Patent Application No. PCT/IN2013/000679, dated Feb. 24, 2014.
International Written Opinion of the International Searching Authority for International Patent Application No. PCT/IN2013/000679, dated Feb. 24, 2014.
XP-002720094; Database Caplus (Online); Feb. 6, 2012; pp. 1-6; Chemical Abstracts Service, Columbus, Ohio, USA.
Shah, et al.; Synthesis of New Bergenin Derivatives as Potent Inhibitors of Inflammatory Mediators NO and TNF~α; 2012; pp. 2744-2747; vol. 22; Bioorganic & Medicinal Chemistry Letters.

*Primary Examiner* — Nyeemah A Grazier
(74) *Attorney, Agent, or Firm* — McDonald Hopkins LLC

(57) ABSTRACT

The present invention relates to 2,3,4,4a-tetrahydro-3,4,8,10-tetrahydroxy-2-(hydroxymethyl)-9-methoxypyrano[3,2-c]isochromen-6(10bH)-one analogs of the Formula I, wherein, R, R' and R" are as herein described. In addition, the invention relates to methods of using compounds for treating or preventing various inflammatory disorders such as rheumatoid arthritis, inflammatory bowel disease, psoriasis, asthma and chronic obstructive pulmonary disorder.

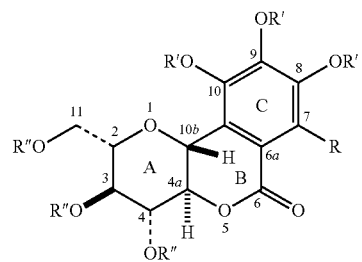

18 Claims, 2 Drawing Sheets

TETRAHYDRO-2H-PYRANO[3,2-C] ISOCHROMENE-6-ONES AND ANALOGS FOR THE TREATMENT OF INFLAMMATORY DISORDERS

This application is a 35 U.S.C. 371 national stage filing and claims priority to PCT Application No. PCT/IN2013/000679, entitled "TETRAHYDRO-2H-PYRANO[3,2-C] ISOCHROMENE-6-ONES AND ANALOGS FOR THE TREATMENT OF INFLAMMATORY DISORDERS" filed on Nov. 1, 2013, which claims priority to Indian Application No. 1565/DEL/2013 filed on May 24, 2013, both of which are incorporated by reference herein in their entirety.

FIELD OF THE INVENTION

The present invention relates to tetrahydro-2H-Pyrano[3,2-C]isochromene-6-ones. The present invention particularly relates to synthesis and anti-inflammatory activity of 2,3,4,4a-tetrahydro-3,4,8,10-tetrahydroxy-2-(hydroxymethyl)-9-methoxypyrano[3,2-c]isochromen-6(10bH)-one compounds. The present invention also relates to method for treatment of inflammatory diseases, including those caused by elevated levels of proinflammatory cytokines such as tumor necrosis factor-alpha (TNF-α) and/or interleukins (IL-1β, IL-6 or IL-8). Compounds of the invention can be used for prevention or in the treatment of inflammatory diseases, such as rheumatoid arthritis.

BACKGROUND OF THE INVENTION

The human immune response is regulated by a highly complex and intricate network of control elements. Prominent among these regulatory components are the anti-inflammatory cytokines and specific cytokine inhibitors. Under physiologic conditions, these cytokine inhibitors serve as immunomodulatory elements that limit the potentially injurious effects of sustained or excess inflammatory reactions. It has been demonstrated that proinflammation has an association with pathophysiology and is connected with various clinical disease manifestations (Kalogeropoulos et al. *J. Am. Coll. Cardiol.* 2010, 55, 2129). Several dominant proinflammatory cytokines, such as interleukin-6 (IL-6) and tumor necrosis factor-alpha (TNF-α), are involved in the pathogenesis of cardiovascular and nuerodegenerative diseases and cancers through a series of cytokine signaling pathways. Over-expression of cytokines in both mRNA and protein levels is responsible for a number of pathological conditions like ulcerative colitis, diabetes, atherosclerosis, stroke, Alzheimer's disease, and cancer (Ait-Oufella et al. *Arterioscler. Thromb. Vasc. Biol.* 2011, 31, 969; Grivennikov and Karin, *Ann. Rheum. Dis.* 2011, 70, i104). Several cytokines, such as TNF-α, IL-6, and IL-1β, have received a considerable amount of attention as molecular targets for treatment of diseases mentioned above. The inhibition of cytokines, particularly TNF-α, has been successful in several clinical trials for treatment of cancer and rheumatoid arthritis. In addition, it is believed that mast cells, neutrophils, and macrophages which secrete inflammatory factors are the important players in inflammatory disorders. Inhibition of release of cytokines in activated macrophages has become a focus of current drug discovery and development and an important method for evaluating the bioactivity of drugs (Jeremy S. D. *Sem. Nephrol.* 2010, 30, 234).

OBJECTIVES OF THE INVENTION

An object of the present invention is to provide tetrahydro-2H-Pyrano[3,2-C]isochromene-6-ones.

Another objecti of the present invention is to provide novel anti-inflammatory compounds for treatment of inflammatory diseases, such as rheumatoid arthritis.

Still another object of the invention is to provide a process for the preparation of tetrahydro-2H-pyrano[3,2-C]isochromene-6-ones.

SUMMARY OF THE INVENTION

Accordingly the present invention provides a compound represented by formula I or pharmaceutically acceptable salt thereof,

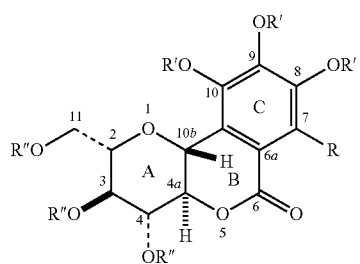

wherein,
R is selected from the group consisting of alkylamino and alkyl,
  wherein the alkylamino is selected from the group consisting of —NH-alkyl, N-dialkyl, NH-cycloalkyl, substituted or unsunstituted N-cycloalkyl and any alkyl substituted amino derived group derived from amino acid or heterocycles like piperidine or morpholine,
  the alkyl is selected from the group consisting of ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl and ($C_6$-$C_{10}$)-bicycloalkenyl; and
R' and R" are each independently selected from the group consisting of hydrogen and alkyl,
  wherein the alkyl is selected from $C_1$-$C_{10}$ carbon chain or branched radical having up to 6 and, preferably up to 5 carbon atoms.

In an embodiment of the present invention, the compound of formula I is selected from the group consisting of

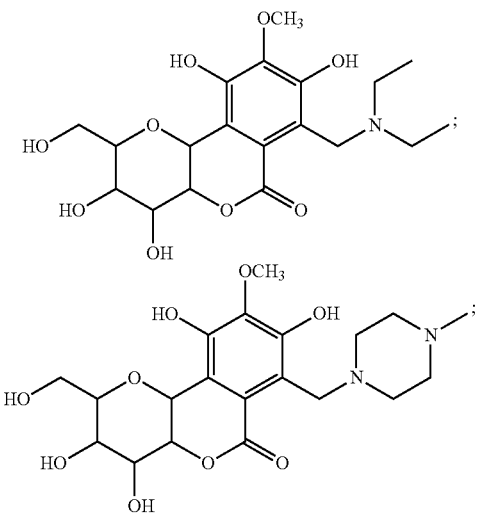

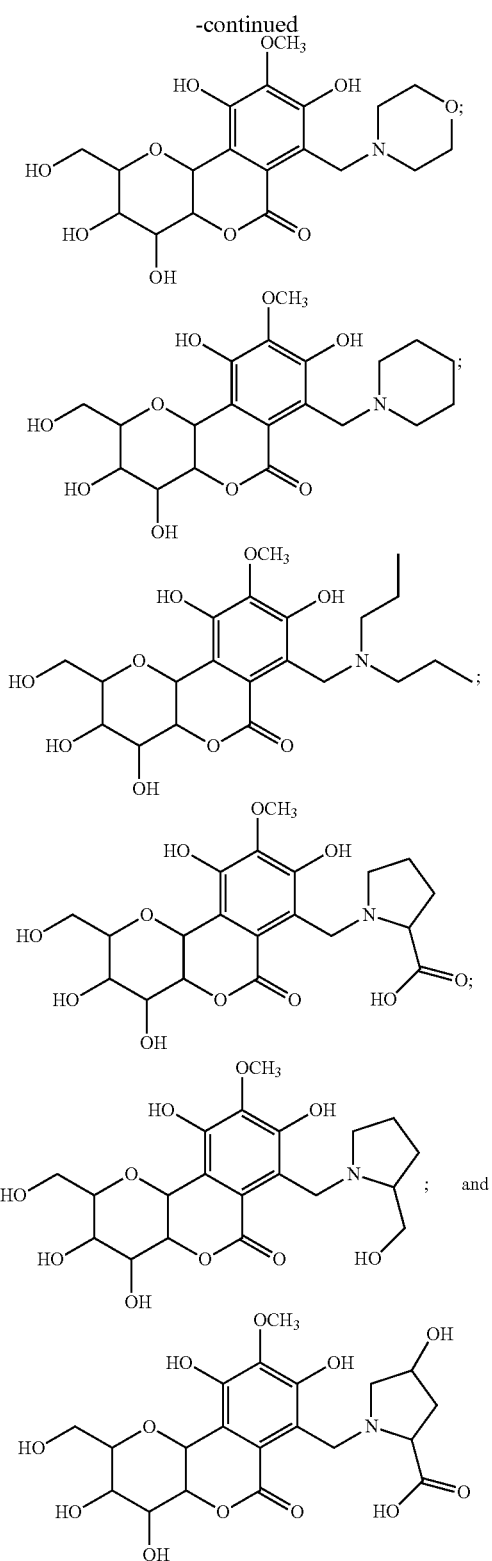

An embodiment of the invention provides a compound of formula I for use in the treatment of inflammatory disorders.

Accordingly, the present invention provides a process for preparation of a compound of formula I, the process comprising: (a) reacting bergenin with formaldehyde and an amino compound in a solvent selected from the group consisting of DMSO and water-alcohol mixture, or reacting bergenin with potassium hydroxide and an alkyl halide in water, to obtain a reaction mixture; (b) passing the reaction mixture through a resin to obtain a compound of formula I and purifying the compound by chromatographic methods.

In another embodiment of the present invention, bergenin is allowed to react with formaldehyde and an amino compound at temperature ranging between 25-50° C. for 6-10 hours.

In yet another embodiment of the present invention, bergenin is allowed to react with potassium hydroxide and an alkyl halide at temperature ranging between 60-100° C. for 6-10 hours.

In an embodiment of the present invention, the alcohol used in water-alcohol mixture is selected from a group consisting of methanol and ethanol.

In another embodiment of the present invention, the ratio of water:alcohol in the mixture is in the range of 1:1 to 1:5.

In still another embodiment of the present invention, the amino compound is selected from a group consisting of proline, prolinol, 4-hydroxy proline, morpholine, piperidine, N-methyl piperazine, diethylamine, di-isopropylamine and pyrrolidine.

In another embodiment of the present invention, the alkyl halide is selected from the group consisting of methyl iodide, ethyl bromide, propyl bromide, n-butyl bromide, isobutyl bromide, isovaleryl chloride, n-pentyl bromide, and other long-chain aliphatic alkyl halides containing carbon chain length up to 20 carbons.

In yet another embodiment of the present invention, the purification of compound of formula I is carried out using saphadex.

An embodiment of the present invention provides a pharmaceutical composition for treatment of inflammatory disorder comprising an effective amount of a compound of formula I along with pharmaceutically acceptable excipients or diluents.

In an embodiment of the present invention, the ratio of the compound is ranging between 1:99 to 50:50.

In yet another embodiment of the present invention, the pharmaceutically acceptable excipient is selected from a group consisting of saccharides (such as lactose, starch, dextrose), stearates (such as stearic acid, magnesium stearate), polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates (such as sodium carbonate, sodium bicarbonate) and talc.

Another embodiment of the present invention provides a method for treating or preventing development of an inflammatory disease comprising administering to a patient suffering from or at the risk of developing a inflammatory disease, a therapeutically-effective amount of a compound represented by the formula I:

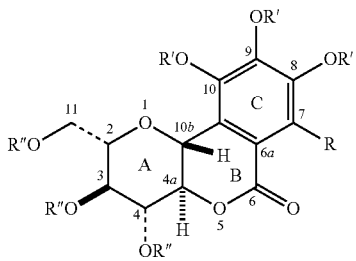

wherein,

R is selected from the group consisting of alkylamino and alkyl,
  wherein the alkylamino is selected from the group consisting of —NH-alkyl, N-dialkyl, NH-cycloalkyl, substituted or unsubstituted N-cycloalkyl and any alkyl substituted amino derived group derived from amino acid or heterocycles like piperidine or morpholine,
  the alkyl is selected from the group consisting of ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl and ($C_6$-$C_{10}$)-bicycloalkenyl; and R' and R" are each independently selected from the group consisting of hydrogen and alkyl,
  wherein the alkyl is selected from $C_1$-$C_{10}$ carbon chain or branched radical having up to 6 and, preferably up to 5 carbon atoms.

In an embodiment of the present invention, the patient is a human.

In yet another embodiment of the present invention, the inflammatory disease is selected from the group consisting of rheumatoid arthritis, inflammatory bowel disease, psoriasis, asthma and chronic obstructive pulmonary disorder.

In still another embodiment of the present invention, the inflammatory disease is rheumatoid arthritis.

Chemical synthesis of the 2,3,4,4a-tetrahydro-3,4,8,10-tetrahydroxy-2-(hydroxymethyl)-9-methoxypyrano[3,2-c]isochromen-6(10bH)-one analogs 2-9

Figure 2:
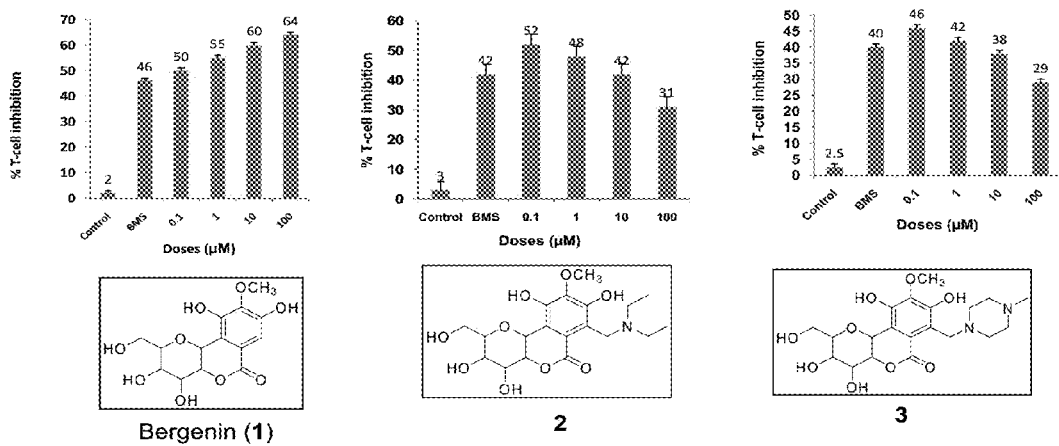

FIG. 2 is a diagram showing in vitro effect of bergenin and its derivatives on T-cell proliferation.

In-vitro effect of 2,3,4,4a-tetrahydro-3,4,8,10-tetrahydroxy-2-(hydroxymethyl)-9-methoxypyrano[3,2-c]isochromen-6(10bH)-one analogs 1-3 on T-cell Proliferation (positive control is BMS, that is betamethasone)

Figure 3:
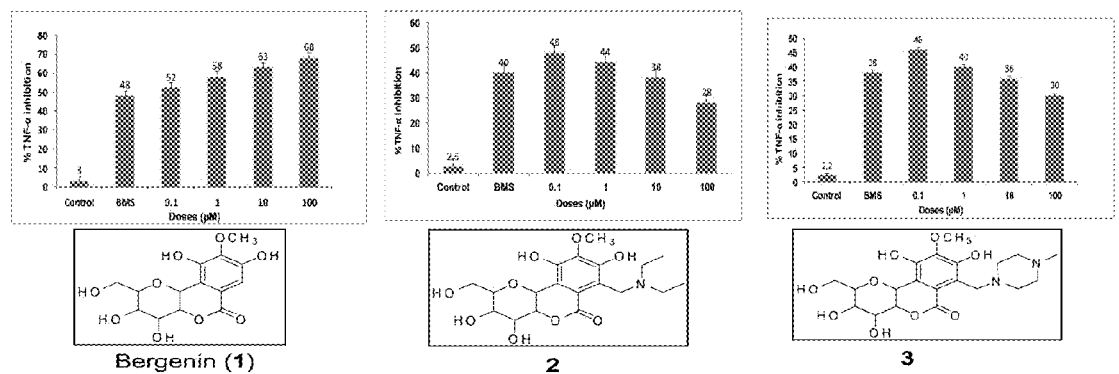

FIG. 3 is a diagram showing in vitro effect of bergenin and its derivatives on TNF-α production.

In vitro effect of 2,3,4,4a-tetrahydro-3,4,8,10-tetrahydroxy-2-(hydroxymethyl)-9-methoxypyrano[3,2-c]isochromen-6(10bH)-one analogs 1-3 on TNF-α production (positive control is BMS, that is betamethasone)

Figure 4:
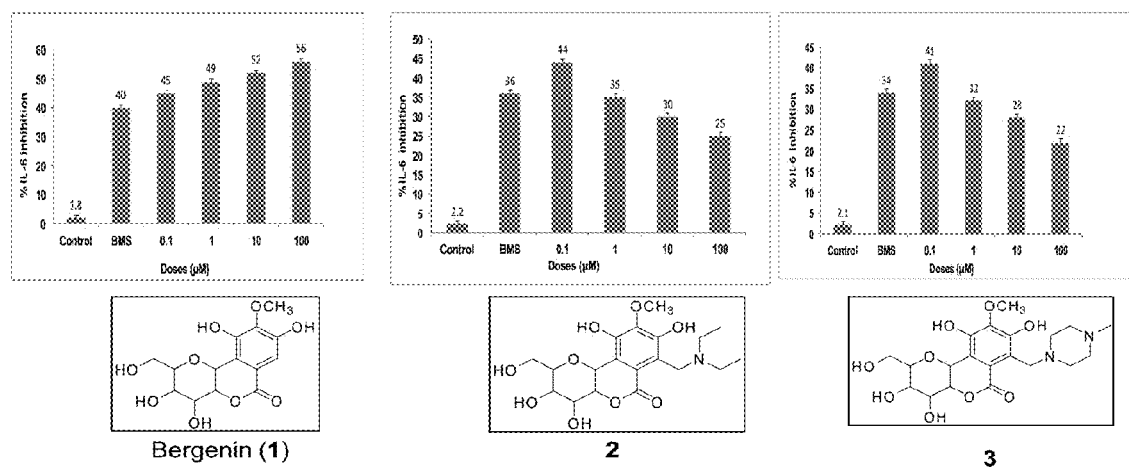

FIG. 4 is a diagram showing in vitro effect of bergenin and its derivatives on IL-6 production.

In vitro effect of 2,3,4,4a-tetrahydro-3,4,8,10-tetrahydroxy-2-(hydroxymethyl)-9-methoxypyrano[3,2-c]isochromen-6(10bH)-one analogs 1-3 on IL-6 production (positive control is BMS that is betamethasone)

DETAILED DESCRIPTION OF THE INVENTION

The present invention provides 2,3,4,4a-tetrahydro-3,4,8,10-tetrahydroxy-2-(hydroxymethyl)-9-methoxypyrano[3,2-c]isochromen-6(10bH)-one compounds (general structure shown below) as promising anti-inflammatory agents.

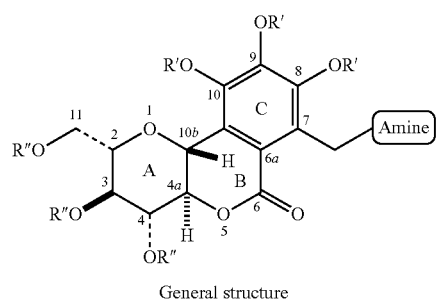

General structure

The present invention relates to novel compounds that show promising anti-inflammatory effects via inhibition of T-cell proliferation and inhibition of cytokines involved in inflammatory diseases (e.g. TNF-alpha, IL-1β, IL-6 etc.). The effect of bergenin and its semisynthetic derivatives on T-cell proliferation ($IC_{50}$: 1=0.1 μM, 2=<0.1 μM, 3=6.1 μM), TNF-α production inhibition ($IC_{50}$: 1=0.63 μM, 2=<0.1 μM, 3=0.1 μM) and IL-6 production inhibition ($IC_{50}$: 1=<0.1 μM, 2=<0.1 μM, 3=0.1 μM) is shown in FIGS. 2-4, respectively. Table 1 shows $IC_{50}$ values of bergenin (1) and compounds 2-3 for inhibition of T-cell proliferation and TNF-α/IL-6 production, which clearly indicates superiority of compounds 2-3 over parent natural product bergenin (1). As shown in Table 1, compounds 2 and 3 showed >6-fold better activity against TNF-α inhibition. The effect of compounds 1-3 on cytokine (TNF-α/IL-6) levels in supernatant and serum of macrophages in in-vivo LPS (Lipopolysaccharide) induced model is provided in Table 2 and 3. Both new compounds 2 and 3 showed better activity than bergenin (1) against TNF-α in this model (Table 3). The inhibitory properties of compounds of the invention can, therefore, be used to treat or prevent diseases, disorders, conditions, or symptoms in a patient (e.g. human) that involve, directly, or indirectly, cytokine over-expression or proliferation of T-cells.

A class of bergenin derivatives is presented and defined by structural formula I:

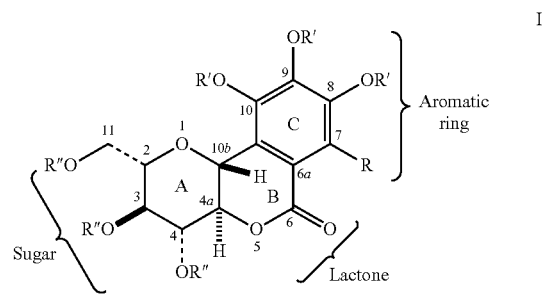

wherein
R is selected from the group consisting of alkylamino and alkyl,
  wherein the alkylamino is selected from the group consisting of —NH-alkyl, N-dialkyl, NH-cycloalkyl, substituted or unsubstituted N-cycloalkyl and any alkyl substituted amino derived group derived from amino acid or heterocycles like piperidine or morpholine,
  the alkyl is selected from the group consisting of ($C_1$-$C_6$)-alkyl, ($C_1$-$C_4$)-haloalkyl, ($C_1$-$C_4$)-alkoxy, ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl and ($C_6$-$C_{10}$)-bicycloalkenyl; and R' and R" are each independently selected from the group consisting of hydrogen and alkyl,
wherein the alkyl is selected from $C_1$-$C_{10}$ carbon chain or branched radical having up to 6 and, preferably up to 5 carbon atoms.

Compounds of the present invention derived from Formula I include, but are not limited to, the following chemical structures:

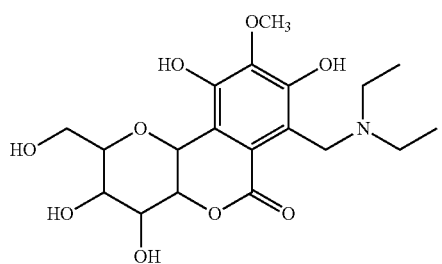 [SMILES: CCN(CC)Cc1c(O)c(OC)c(O)c2c1C(=O)OC1C2OC(CO)C(O)C1O]

7-((Diethylamino)methyl)-2,3,4,4a-tetrahydro-3,4,8,10-tetrahydroxy-2-(hydroxymethyl)-9-methoxy-pyrano[3,2-c]isochromen-6(10bH)-one; Compound 2

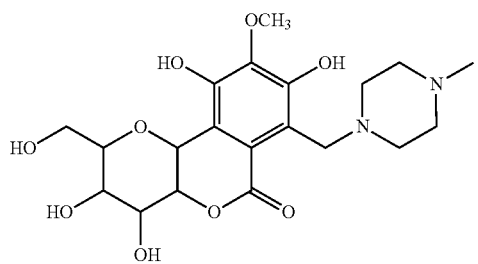 [SMILES: COc1c(O)c(CN2CCN(C)CC2)c2c(c1O)C1OC(CO)C(O)C(O)C1OC2=O]

2,3,4,4a-Tetrahydro-3,4,8,10-tetrahydroxy-2-(hydroxymethyl)-9-methoxy-7-((4-methylpiperazin-1-yl)methyl)pyrano[3,2-c]isochromen-6(10bH)-one; Compound 3

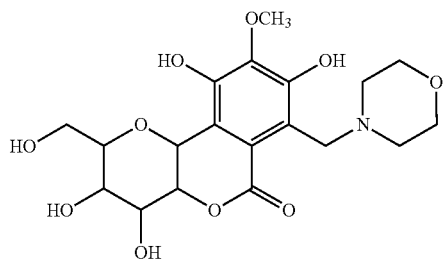 [SMILES: COc1c(O)c(CN2CCOCC2)c2c(c1O)C1OC(CO)C(O)C(O)C1OC2=O]

2,3,4,4a-Tetrahydro-3,4,8,10-tetrahydroxy-2-(hydroxymethyl)-9-methoxy-7-(morpholinomethyl)pyrano[3,2-c]isochromen-6(10bH)-one; Compound 4

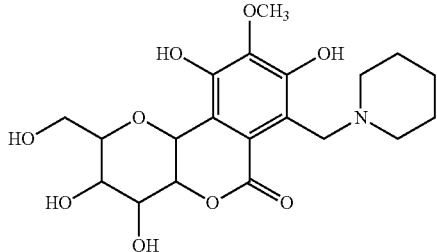 [SMILES: COc1c(O)c(CN2CCCCC2)c2c(c1O)C1OC(CO)C(O)C(O)C1OC2=O]

2,3,4,4a-Tetrahydro-3,4,8,10-tetrahydroxy-2-(hydroxymethyl)-9-methoxy-7-((piperidin-1-yl)methyl)pyrano[3,2-c]isochromen-6(10bH)-one; Compound 5

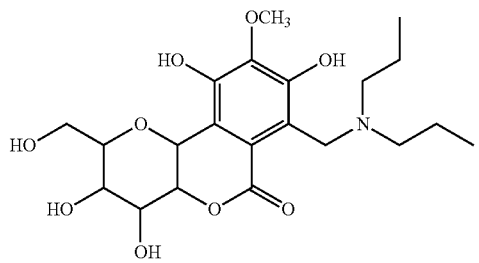 [SMILES: CCCN(CCC)Cc1c(O)c(OC)c(O)c2c1C(=O)OC1C2OC(CO)C(O)C1O]

7-((Dipropylamino)methyl)-2,3,4,4a-tetrahydro-3,4,8,10-tetrahydroxy-2-(hydroxymethyl)-9-methoxy-pyrano[3,2-c]isochromen-6(10bH)-one; Compound 6

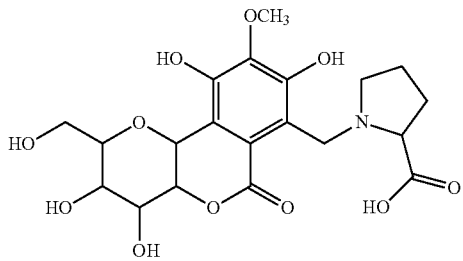 [SMILES: COc1c(O)c(CN2CCCC2C(=O)O)c2c(c1O)C1OC(CO)C(O)C(O)C1OC2=O]

1-((2,3,4,4a,6,10b-Hexahydro-3,4,8,10-tetrahydroxy-2-(hydroxymethyl)-9-methoxy-6-oxopyrano[3,2-c]isochromen-7-yl)methyl)pyrrolidine-2-carboxylic acid; Compound 7

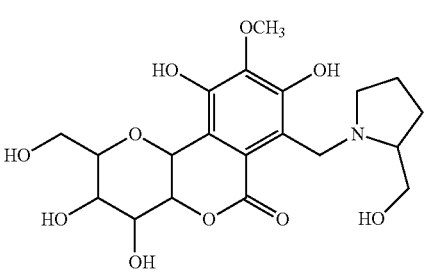 [SMILES: COc1c(O)c(CN2CCCC2CO)c2c(c1O)C1OC(CO)C(O)C(O)C1OC2=O]

2,3,4,4a-Tetrahydro-3,4,8,10-tetrahydroxy-2-(hydroxymethyl)-7-((2-(hydroxymethyl)pyrrolidin-1-yl)methyl)-9-methoxypyrano[3,2-c]isochromen-6(10bH)-one; Compound 8

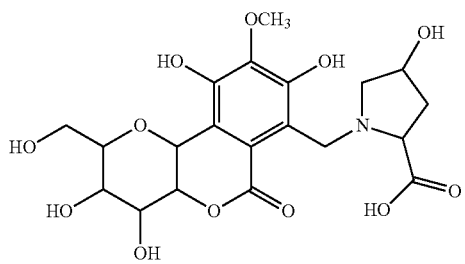 [SMILES: COc1c(O)c(CN2CC(O)CC2C(=O)O)c2c(c1O)C1OC(CO)C(O)C(O)C1OC2=O]

1-((2,3,4,4a,6,10b-Hexahydro-3,4,8,10-tetrahydroxy-2-(hydroxymethyl)-9-methoxy-6-oxopyrano[3,2-c]isochromen-7-yl)methyl)-4-hydroxypyrrolidine-2-carboxylic acid; Compound 9

As used herein, the terms below have the meanings as indicated.

The term "alkoxy," as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical optionally substituted containing from 1 to 20 and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkylamino" as used herein, alone or in combination, refers to an alkyl group optionally substituted attached to the parent molecular moiety through an amino group. Alkylamino groups may be mono- or dialkylated, forming groups such as, for example, N-methylamino, N-ethylamino, N,N-dimethylamino, N,N-ethylmethylamino and the like.

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl" as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstitutedsilyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." Asymmetric centers exist in the compounds of the present invention. These centers are designated by the symbols "R" or "S" depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the way they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diastereoisomers differ not only in the way they rotate plane polarized light, but also their physical properties. The term "optical isomer" comprises more particularly the enantiomers and the diastereoisomers, in pure form or in the form of a mixture.

The term "inflammatory disease" as used herein refers to any disease, disorder, condition, or symptom characterized by the inflammation of the organ or part of the body. Inflammatory diseases include, e.g., rheumatoid arthritis, inflammatory bowel disease, psoriasis, asthma and chronic obstructive pulmonary disorder.

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, rabbits, and rodents (e.g., rats, mice, and guinea pigs).

Inflammatory diseases. One or more compounds of the invention can be used to treat a patient (e.g. a human) at a risk of developing or already suffering from a inflammatory disease, such as rheumatoid arthritis, inflammatory bowel disease, psoriasis, asthma and chronic obstructive pulmonary disorder.

Cell derived inflammatory mediators may include lysozyme granules, histamine, interferon-gamma, interleukins IL-1β, IL-4, IL-6, nitric oxide, prostaglandins and TNF-α.

Methods of Prevention and Treatment.

The compounds of the invention can be used to treat a patient (e.g. a human) that suffers from or is at a risk of suffering from a disease, disorder, condition, or symptom described herein. The compounds of the invention can be used alone or in combination with other agents and compounds in methods of treating or preventing e.g. a inflammatory disease (e.g. rheumatoid arthritis). Each such treatment described above includes the step of administering to a patient in need thereof a therapeutically effective amount of the compound of the invention described herein to delay, reduce or prevent such a disease, disorder, condition, or symptom. The compounds of the invention presented herein may be also useful in reducing inflammation of various organs, joints and the like.

Besides being useful for human treatment, the compounds of the present invention will also be useful for the treatment of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

It is understood that the foregoing examples are merely illustrative of the present invention. Certain modifications of the articles and/or methods employed may be made and still achieve the objectives of the invention. Such modifications are contemplated as within the scope of the claimed invention.

EXAMPLES

Example 1

Bergenin (1)

Commercially available bergenin was purchased. White crystalline solid; m.p. 234-235° C.; $^1$H NMR (DMSO-$d_6$, 400 MHz): δ 7.07 (s, 1H, Ar—H), 4.96 (d, J=10.4 Hz, 1H, 10b), 3.99 (dd, 1H, H-4a), 3.82 (dd, 1H, H-4), 3.77 (s, 3H, OCH$_3$), 3.59 (dd, 1H, H-11a), 3.55 (m, 1H, H-2), 3.43 (dd, 1H, H-11b), 3.19 (dd, 1H, H-3); ESI-MS: m/z 329 [M+1]$^+$.

Example 2

Synthesis of 7-((Diethylamino)methyl)-2,3,4,4a-tetrahydro-3,4,8,10-tetrahydroxy-2-(hydroxymethyl)-9-methoxypyrano[3,2-c]isochromen-6(10bH)-one (Compound 2)

Figure 1:
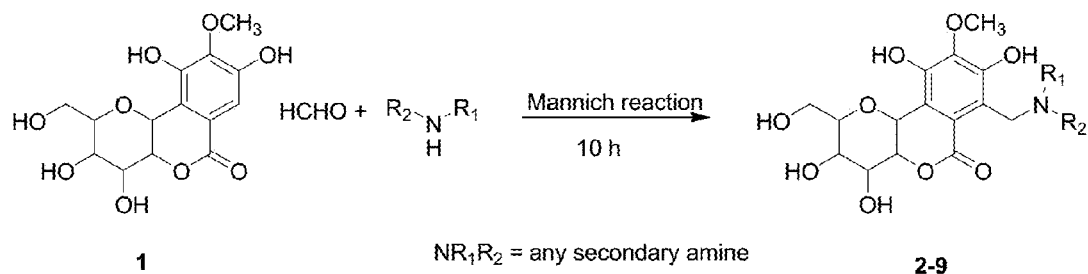
FIG. 1 is a diagram illustrating the chemical synthesis of the bergenin derivatives of the invention.

A general synthetic strategy for compounds (2-9) proposed in present invention is depicted in FIG. 1. Synthesis of compounds (2-9) proceeds smoothly in polar solvents such as DMSO or water:alcohol mixture (water:methanol or water: ethanol) at 25-50° C. in 6-10 h. The conditions used in the synthesis are mild and yields are excellent. The method of synthesis for compounds of the invention is as follows: To the solution of bergenin (32 mg, 1 mmol) in DMSO (2 mL), 37% formaldehyde solution (0.5 mL) and one equivalent of diethylamine (1 mmol) was added. The solution was stirred at 25° C. for 8 h, and the mixture was diluted with water and passed through HP20 resin bed to remove DMSO and then it was purified over sephadex LH-20 in methanol to get pure compound 2. White powder; m.p. 144-146° C.; $^1$H NMR (DMSO-$d_6$, 500 MHz): δ 4.96 (d, J=10.4 Hz, 1H, H-10b), 4.02 (m, 3H, H-4,4a,11), 3.99 (m, 4H, OCH$_3$, H-11), 3.80 (m, 2H, H-2,3), 3.41 (m, 2H, H-12) 2.93 (m, 4H, 2×N—CH$_2$), 1.23 (t, 6H, 2×CH$_3$); ESI-MS: m/z 414 [M+1]$^+$.

Example 3

Synthesis of 2,3,4,4a-tetrahydro-3,4,8,10-tetrahydroxy-2-(hydroxymethyl)-9-methoxy-7-((4-methylpiperazin-1-yl)methyl)pyrano[3,2-c]isochromen-6(10bH)-one (Compound 3)

To the solution of bergenin (32 mg, 1 mmol) in DMSO (2 mL), 37% formaldehyde solution (0.5 mL) and one equivalent of N-methyl piperazine (1 mmol) was added. The solution was stirred at 25° C. for 8 h, and the mixture was diluted with water and passed through HP20 resin bed to remove DMSO and then it was purified over sephadex LH-20 in methanol to get pure compound 3. White powder; m.p. 204-207° C.; $^1$H-NMR (CD$_3$OD, 200 MHz): δ 4.93 (d, J=8.6 Hz, 1H, H-10b), 4.25 (m, 1H, H-11a), 4.02 (s, 3H, OCH$_3$), 3.91 (brs, 4, 2H, H-11b), 3.80 (m, 1H, H-2), 3.55 (m, 2H, H-3, H-4), 3.05 (m, 2H, H-12), 2.79 (m, 4H, H-2', H-6'), 2.57 (brs, 4H, H-3', H-5'), 2.34 (s, 3H, N—CH₃); ESI-MS: m/z 441 [M+1]⁺.

Example 4

Synthesis of 2,3,4,4a-tetrahydro-3,4,8,10-tetrahydroxy-2-(hydroxymethyl)-9-methoxy-7-(morpholinomethyl)pyrano[3,2-c]isochromen-6(10bH)-one (Compound 4)

To the solution of bergenin (32 mg, 1 mmol) in DMSO (2 mL), 37% formaldehyde solution (0.5 mL) and one equivalent of morpholine (1 mmol) was added. The solution was stirred at 40° C. for 8 h, and the mixture was diluted with water and passed through HP20 resin bed to remove DMSO and then it was purified over sephadex LH-20 in methanol to get pure compound 4. White powder; m.p. 191-193° C.; ¹H-NMR (DMSO-d₆, 500 MHz): δ 4.65 (d, J=9.6 Hz, 1H, H-10b), 4.59 (dd, 1H, H-4a), 4.26 (dd, 1H, H-11b), 4.18 (m, 1H, H-3), 3.70 (s, 3H, OCH₃), 3.74-3.60 (m, 7H, H-2, H-4, H-11b, H-3', H-5'), 3.27 (m, 3H, H-2', H-12a), 2.88 (m, 3H, H-6, H-12b); ESI-MS: m/z 428 [M+1]⁺.

Example 5

Synthesis of 2,3,4,4a-tetrahydro-3,4,8,10-tetrahydroxy-2-(hydroxymethyl)-9-methoxy-7-((piperidin-1-yl)methyl)pyrano[3,2-c]isochromen-6(10bH)-one (Compound 5)

To the solution of bergenin (32 mg, 1 mmol) in DMSO (2 mL), 37% formaldehyde solution (0.5 mL) and one equivalent of piperidine (1 mmol) was added. The solution was stirred at 40° C. for 8 h, and the mixture was diluted with water and passed through HP20 resin bed to remove DMSO and then it was purified over sephadex LH-20 in methanol to get pure compound 5. White powder; m.p. 218-220° C.; ¹H-NMR (DMSO-d₆, 400 MHz): δ 4.89 (d, J=9.6 Hz, 1H, H-10b), 4.10 (m, 2H, H-1a, H-4a), 3.95 (m, 1H, H-4), 3.90 (m, 1H, H-11b), 3.54 (s, 3H, OCH₃), 3.62 (m, 2H, H-12), 3.34 (m, 1H, H-2), 3.17 (m, 1H, H-3), 2.50 (brs, 4H, H-2', H-6'), 1.55 (br s, 4H, H-3', H-5'), 1.44 (brs, 2H, H-4'); ESI-MS: m/z 426 [M+1]⁺.

Example 6

Synthesis of 7-((dipropylamino)methyl)-2,3,4,4a-tetrahydro-3,4,8,10-tetrahydroxy-2-(hydroxymethyl)-9-methoxypyrano[3,2-c]isochromen-6(10bH)-one (Compound 6)

To the solution of bergenin (32 mg, 1 mmol) in water: methanol (1:1; 2 mL), 37% formaldehyde solution (0.5 mL) and one equivalent of di-propylamine (1 mmol) was added. The solution was stirred at 50° C. for 10 h, and the mixture was diluted with water and passed through HP20 resin bed to remove DMSO and then it was purified over sephadex LH-20 in methanol to get pure compound 6. Cream colored solid; m.p. 116-118° C.; ¹H-NMR (DMSO-d₆, 500 MHz): δ 4.90 (d, J=10.3 Hz, 1H, H-10b), 4.19 (dd, 1H, H-11a), 4.11 (dd, 1H, H-4), 4.94 (m, 1H, H-4a), 3.80 (m, 1H, H-3), 3.70 (s, 3H, OCH₃), 3.62 (m, 1H, H-11b), 3.58 (m, 1H, H-2), 3.19 (m, 2H, H-12), 2.48 (brs, 4H, N—CH₂), 1.50 (brs, 4H, N—CH₂—CH₂), 0.84 (brs, 6H, —CH₂—CH₃); ESI-MS m/z: 442 [M+1]⁺.

Example 7

Synthesis of 1-((2,3,4,4a,6,10b-hexahydro-3,4,8,10-tetrahydroxy-2-(hydroxymethyl)-9-methoxy-6-oxopyrano[3,2-c]isochromen-7-yl)methyl)pyrrolidine-2-carboxylic acid (Compound 7)

To the solution of bergenin (32 mg, 1 mmol) in water: methanol (1:1; 2 mL), 37% formaldehyde solution (0.5 mL) and one equivalent of proline (1 mmol) was added. The solution was stirred at 50° C. for 8 h, and the mixture was diluted with water and passed through HP20 resin bed to remove DMSO and then it was purified over sephadex LH-20 in methanol to get pure compound 7. White needles; m.p. 204-206° C.; ¹H-NMR (DMSO-d₆, 500 MHz): δ 5.00 (d, J=10.4 Hz, 1H, H-10b), 4.30 (m, 2H, H-4, H-4a), 4.00 (t, 1H, H-4), 3.97 (dd, 1H, H-11b), 3.80 (S, 3H, OCH₃), 3.70 (m, 2H, H-2, H-3), 3.5 (m, 1H, H-5'a) 3.21 (m, 3H, H-5'b, H-12), 3.04 (m, 1H, H-2'a), 2.21 (m, 1H, H-3'b), 2.06 (m, 1H, H-3'a), 1.92 (m, 1H, H-4'b), 1.69 (m, 1H, H-4'a); ESI-MS: m/z 456 [M+1]⁺.

Example 8

Synthesis of 2,3,4,4a-tetrahydro-3,4,8,10-tetrahydroxy-2-(hydroxymethyl)-7-((2-(hydroxymethyl)pyrrolidin-1-yl)methyl)-9-methoxypyrano[3,2-c]isochromen-6(10bH)-one (Compound 8)

To the solution of bergenin (32 mg, 1 mmol) in water: ethanol (1:1; 2 mL), 37% formaldehyde solution (0.5 mL) and one equivalent of prolinol (1 mmol) was added. The solution was stirred at 40° C. for 8 h, and the mixture was diluted with water and passed through HP20 resin bed to remove DMSO and then it was purified over sephadex LH-20 in methanol to get pure compound 8. White powder; m.p. 194-196° C.; ¹H-NMR (DMSO-d₆, 500 MHz): δ 4.50 (d, J=10 Hz, 1H, H-10b), 3.78 (brs, 1H, H-11a), 3.71 (m, 2H, H-4, H-11b), 3.59 (m, 2H, H-6'), 3.54 (brs, 4H, OCH₃, H-4a), 3.16 (m, 2H, H-2, H-3), 2.71 (S, 2H, H-12), 2.50 (brs, 3H, H-5', H-2'), 2.10 (m, 1H, H-3'b), 2.04 (m, 1H, H-3'a), 1.90 (m, 1H, H-4'b), 1.71 (m, 1H, H-4'a); ESI-MS: m/z 442 [M+1]⁺.

Example 9

Synthesis of 1-((2,3,4,4a,6,10b-hexahydro-3,4,8,10-tetrahydroxy-2-(hydroxymethyl)-9-methoxy-6-oxopyrano[3,2-c]isochromen-7-yl)methyl)-4-hydroxypyrrolidine-2-carboxylic acid (Compound 9)

To the solution of bergenin (32 mg, 1 mmol) in water: ethanol (1:1; 2 mL), 37% formaldehyde solution (0.5 mL) and one equivalent of 4-hydroxy proline (1 mmol) was added. The solution was stirred at 40° C. for 8 h, and the mixture was diluted with water and passed through HP20 resin bed to remove DMSO and then it was purified over sephadex LH-20 in methanol to get pure compound 9. White crystals; m.p. 217-219° C.; ¹H-NMR (DMSO-d₆, 500 MHz): δ 4.99 (d, J=10.3 Hz, 1H, H-10b), 4.46 (dd, 1H, H-11a), 4.37 (dd, 1H, H-4a), 4.27 (brs, 1H, H-4'), 3.94 (m, 1H, H-4), 3.86 (m, 1H, H-11a), 3.79 (s, 3H, OCH₃), 3.60 (m, 2H, H-2, H-3), 3.17 (m, 2H, H-12), 2.98 (dd, 1H, H-2'), 2.67 (brs, 1H, H-5'a), 2.36 (brs, 1H, H-5'a), 2.08 (m, 2H, H-3'); ESI-MS: m/z 472 [M+1]⁺.

Example 10

Effect of Compounds of the Invention on T-Cell Proliferation

Compounds provided in present invention were evaluated for their effect on T-cell proliferation. The protocol used for this bioassay is as follows: A single spleen cell suspension was prepared under sterile conditions and suspended in complete medium RPMI 1640 containing 10% Fetal calf serum (FCS). Spleenocytes were seeded into 4-5 wells of a 96-well flat bottom microtitre plate (Nunc) at ($2 \times 10^6$ cells/ml). Thereafter, Concanavalin (Con-A) in the final concentration of 2.5 µg/well was added to stimulate T-cell, or LPS in the final concentration of 1 µg/ml was added to stimulate B-cell in the respective wells. Variable concentrations of compounds of the present invention (0.1 µM-100 µM) were added. Thereafter, the plates were incubated at 37° C. in 95% humidity at 5% $CO_2$ in a $CO_2$ incubator for 72 hrs. After 72 hours, 50 µl of MTT solution (5 mg/ml) was added to each well and the plates were incubated for 4 h. Thereafter, plates were centrifuged (400×g, 5 min.) and the untransformed MTT was removed. 200 µl of DMSO (192 µl with 8 µl 1N HCl) was added to each well, and the absorbance was determined in an ELISA reader at 570 nm after 15 min (*Life Sci.* 2007, 80, 1525-1538).

Bergenin (1) along with all tested compounds 2-9 showed inhibition of T-cell proliferation. Bergenin (1) and compounds 2 and 3 were most potent. The activity profile of these compounds is shown in FIG. 2 and Table 1.

Example 11

Effect of Compounds of the Present Invention on Pro-Inflammatory Cytokines TNF-α and IL-6 Production Splenocytes were seeded into three to four wells of a 96-well flat-bottom microtiter plate (Nunc) at $2 \times 10^6$ cells/ml. Cells were incubated with different concentrations of compounds (0.1 µM-100 µM) along with Con A (2.5 µg/well) or LPS (1 µg/ml) for 72 h at 37° C. with 5% $CO_2$ in $CO_2$ incubator. The culture supernatants were harvested and the measurement of cytokines (TNF-α and IL-6) in the culture supernatants was carried out using commercial kits as per manufacturer's instructions by using ELISA kits (R&D, USA) (*Life Sci.* 2007, 80, 1525-1538; *J. Immunol. Methods* 1983, 65, 55-63).

Bergenin (1) along with all tested compounds 2-9 showed inhibition of TNF-α, IL-4, IL-1β and IL-6 production at low micromolar to nanomolar concentrations. Bergenin (1) along with compounds 2 and 3 were most potent. The TNF-α and IL-6 inhibition profile of compounds 1-3 is shown in FIG. 3, FIG. 4 and Table 1 respectively.

TABLE 1

$IC_{50}$ values of 2,3,4,4a-tetrahydro-3,4,8,10-tetrahydroxy-2-(hydroxymethyl)-9-methoxypyrano[3,2-c]isochromen-6(10bH)-one compounds 1-3 for inhibition of T-cell proliferation and cytokine production

| | $IC_{50}$ (µM) | | |
|---|---|---|---|
| Compound | T-cell proliferation | TNF-α production | IL-6 production |
| 1 | 0.1 | 0.63 | <0.1 |
| 2 | <0.1 | <0.1 | <0.1 |
| 3 | 6.1 | <0.1 | <0.1 |

Example 12

Effect of Compounds of the Present Invention on Pro-Inflammatory Cytokines TNF-α and IL-6 Production in In-Vivo LPS Model Macrophages are the main source of cytokines in inflammation. Lipopolysaccharides LPS may stimulate macrophages to produce large quantities of proinflammatory cytokines that promote inflammation. In this study, we investigated the effect of compounds 1-3 on the expression and secretion of cytokines (TNF-α/IL-6) in vivo in cell supernatant and serum. For this study, male Balb/c mice (5-6 weeks of age) were maintained under pathogen-free conditions in an animal housing unit in a temperature-controlled (23±2° C.) and light-controlled (12 h light/dark cycle) room. Animals were provided standard rodent chow and water ad libitum. Female Balb/C mice (8-10 weeks) were obtained from animal house, 3 or 4 per cage with a 12 h light/dark cycle, provided standard water ad libitum, and acclimated to their environment at least a week before the start of experiments. One hour prior to the start of each experiment, feed and water were removed from the cages. Mice were treated with 10 mg/kg and 100 mg/kg of compounds 1-3 orally over a period of 5 days. LPS 10 µg/ml was injected and blood as well macrophages were collected. The dose was selected based on in vitro result. Results are shown in Table 2 and 3.

Measurement of in vivo serum levels of TNF-α and IL-6: The mice were divided into 4 groups: no treatment group, injected with phosphate buffered saline (PBS); LPS only; LPS+Dexamethasone (0.05 µg/ml); or LPS+compound 1 at 10 and 100 µM doses (n=6 for each group). Groups were pretreated orally with 200 µl of PBS, dexamethasone or compounds 1, 2, 3 for 45 min. Lipopolysaccharide (100 nM) was then administered (200 µL) i.p for treatment groups, and RPMI was administered i.p for the negative control group. Results are shown in Table 3.

Ex vivo TNF-α and IL-6 determination by ELISA: Blood was allowed to clot overnight at 4° C. Serum was analyzed for IL-6, TNF-α, and IL-1β by ELISA. IL-6 analysis was performed using purified and biotin-conjugated rat anti-mouse IL-6 antibodies from PharMingen (San Diego, Calif.) as described previously. Streptavidin—peroxidase (Sigma) and 3,3',5,5'-tetramethylbenzidine (TMB, Fluka, Ronkonkoma, N.Y.) were used for detection. Absorbance was read at 450 nm using a Vmax™ Kinetic Microplate Reader (Molecular Devices, Menlo Park, Calif.). For TNF-α analysis the OptEIA Set: Mouse TNF-α (Mono/Poly) kit was employed (PharMingen) (*J. Immunol. Methods* 1983, 65, 55-63). Results are shown in Table 3.

Ex vivo determination of TNF-α, IL-6 & IL-1β in cell supernatant: Blood for serum cytokines production was collected from each treated and untreated animals before the collection of macrophages from peritoneal cavity. Cells were seeded in 96-well plates at $5 \times 10^5$ cells $mL^{-1}$. Cells were then stimulated with 1 µg $mL^{-1}$ LPS for 4 hrs. The cell supernatant was stored at −80° C. The production of TNF-α, IL-6, IL-1β and NO in macrophages cell supernatants of LPS-challenged mice were measured by commercial ELISA kits (B. D. Pharmingenin; R&D systems, Inc., Minneapolis, Minn., USA) and cytokine concentration was determined (*J. Am. College Nutr.* 2004, 23, 71-78). Results are shown in Table 2.

Cell viability: Cell viability was monitored by MTT colorimetric assay. Cells were treated with compounds (1-3) for 24 h. One-tenth volume of 5 mg/ml MTT was then added to the culture medium. After 4-h incubation at 37° C., equal cell culture medium volume of 0.04 N HCl in isopropanol was added to disoolve the MTT formazan and the absorbance value was measured using an ELISA plate reader (*J. Ethnopharmacology,* 2011, 135, 545-552).

NO determination by Griess assay: NO production was indirectly assessed by measuring the nitrite level in the cultured media and serum determined by a colorimetric method based on the griess reaction[4]. The cells were incubated with cinnamic aldehyde, cinnamic alcohol, cinnamic acid, coumarin (0, 6.25, 12.5, 25, and 50 μM) in presence of LPS (100 ng/mL) at 37° C. for 24 h. Then, cells were dispensed into 96-well plates, and 100 mL of each supernatant was mixed with the same volume of griess reagent (1% sulfanilamide, 0.1% naphthyl ethylenediamine dihydrochloride and 5% phosphoric acid) and incubated at room temperature for 10 min., the absorbance was measured at 540 nm with a Micro-Reader (Molecular Devices, Orleans Drive, Sunnyvale, Calif.). Serum samples were diluted four times with distilled water and deproteinized by adding 1/20 volume of zinc sulphate (300 g/L) to final concentration of 15 g/L. After centrifugation at 10,000×g for 5 min at room temperature, 100 μL supernatant was applied to a microtitre plate well, followed by 100 μL of Griess reagent. After 10 min of color development at room temperature, the absorbance was measured at 540 nm with a Micro-Reader. By using sodium nitrite to generatea standard curve, the concentration of nitrite was measured by absorbance at 540 nm (*J. Ethnopharmacology,* 2011, 135, 545-552). Results are shown in Table 3.

TABLE 2

Effect of compounds 1-3 on production of TNF-α and IL-6 in cell suparnatant of macrophages in ex vivo LPS-induced model

| Treatment | Dose (μM) | TNF-α (pg/ml) | IL-6 (ng/ml) |
|---|---|---|---|
| Control | — | n.d | n.d |
| LPS | — | 158 ± 13 | 37.9 ± 5.1 |
| Bergenin (1) | 10 | 89 ± 6.1 | 24.6 ± 6.9 |
|  | 100 | 78 ± 4.9 | 53.5 ± 7.5 |
| 2 | 10 | 102 ± 12 | 41.4 ± 8.9 |
|  | 100 | 89 ± 6.4 | 17.3 ± 3.0 |
| 3 | 10 | 78 ± 4.9 | 12.1 ± 2.81 |
|  | 100 | 84 ± 6.7 | 21.1 ± 3.2 | n.d.: not determined

TABLE 3

Effect of compounds 1-3 on production of TNF-α, IL-6 and nitric oxide (NO) in serum in in-vivo LPS-induced model

| Treatment | Dose (μM) | TNF-α (pg/ml) | IL-6 (ng/ml) | NO (μM) |
|---|---|---|---|---|
| Control | — | n.d | n.d | 1.24 ± 0.25 |
| LPS | — | 717 ± 218 | 410 ± 95 | 6.95 ± 1.81 |
| Bergenin (1) | 10 | 667 ± 208 | 282 ± 98 | 2.62 ± 0.62 |
|  | 100 | 509 ± 185 | 55 ± 12 | 3.29 ± 0.88 |
| 2 | 10 | 585 ± 192 | 102 ± 40 | 5.0 ± 0.80 |
|  | 100 | 388 ± 115 | 275 ± 65 | 3.0 ± 0.73 |
| 3 | 10 | 672 ± 221 | 282 ± 98 | 2.87 ± 0.73 |
|  | 100 | 398 ± 62 | 58 ± 12 | 1.24 ± 0.25 | n.d.: not determined

ADVANTAGES OF THE INVENTION

The main advantages of the present invention are:
Compounds of the invention show promising anti-inflammatory effects via inhibition of T-cell proliferation and inhibition of cytokine production at low micromolar to nanomolar concentrations.
Compounds of the invention have good water solubility and are stable.

We claim:

1. A compound represented by formula I or a pharmaceutically acceptable salt thereof,

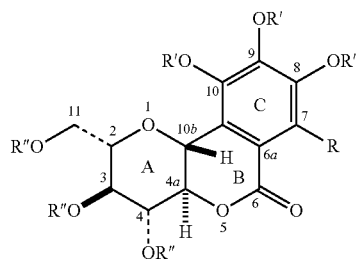

wherein,

R is selected from the group consisting of:
—NH-alkyl, —N-dialkyl, —NH-cycloalkyl, substituted or unsubstituted N-cycloalkyl, an alkyl substituted amino group derived from an amino acid, an alkyl substituted amino group derived from a heterocycle, an alkyl substituted amino group derived from N-dialkyl, an alkyl substituted amino group derived from piperidine, an alkyl substituted amino group derived from morpholine, ($C_1$-$C_6$)-alkyl, ($C_1$-$C_4$)-haloalkyl, ($C_1$-$C_4$)-alkoxy ($C_1$-$C_4$)-haloalkoxy, ($C_5$-$C_8$)-cycloalkyl, ($C_5$-$C_8$)-cycloalkenyl, ($C_6$-$C_{10}$)-bicycloalkyl and ($C_6$-$C_{10}$)-bicycloalkenyl; and R' and R" are each independently selected from the group consisting of hydrogen, a straight or branched $C_1$-$C_{10}$ carbon chain, and a branched radical having up to 6 carbon atoms.

2. The compound as claimed in claim 1, wherein the compound of formula I is selected from the group consisting of:

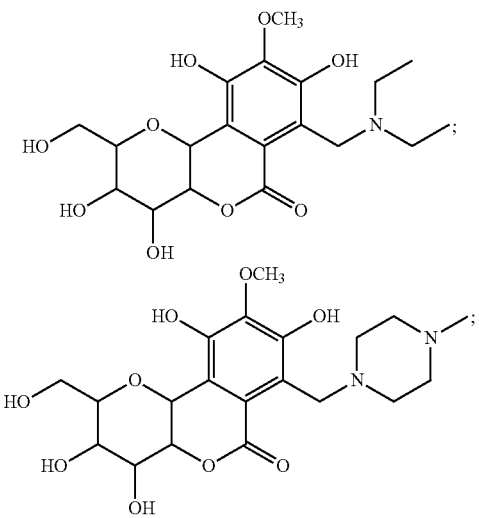

-continued

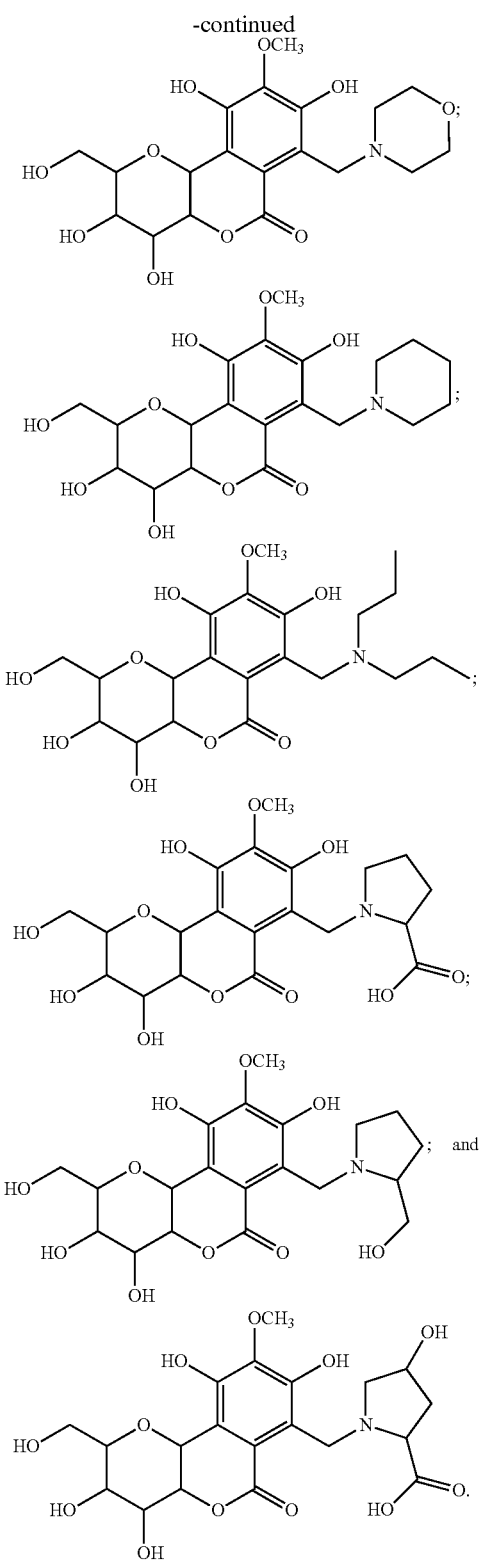

3. A process for preparation of a compound of formula I as claimed in claim 1, said process comprising: (a) reacting bergenin with formaldehyde and an amino compound in a solvent selected from the group consisting of DMSO and water-alcohol mixture, or reacting bergenin with potassium hydroxide and an alkyl halide in water, to obtain a reaction mixture; (b) passing the reaction mixture through a resin to obtain a compound of formula I and purifying the compound by chromatographic methods.

4. The process as claimed in claim 3, wherein bergenin is allowed to react with formaldehyde and an amino compound at temperature ranging between 25-50° C. for 6-10 hours.

5. The process as claimed in claim 3, wherein bergenin is allowed to react with potassium hydroxide and an alkyl halide at temperature ranging between 60-100° C. for 6-10 hours.

6. The process as claimed in claim 3, wherein the alcohol used in water-alcohol mixture is selected from a group consisting of methanol and ethanol.

7. The process as claimed in claim 3, wherein the ratio of water:alcohol in the mixture is in the range of 1:1 to 1:5.

8. The process as claimed in claim 3, wherein the amino compound is selected from a group consisting of proline, prolinol, 4-hydroxy proline, morpholine, piperidine, N-methyl piperazine, diethylamine, di-isopropylamine and pyrrolidine.

9. The process as claimed in claim 3, wherein the alkyl halide is selected from the group consisting of methyl iodide, ethyl bromide, propyl bromide, n-butyl bromide, isobutyl bromide, isovaleryl chloride, n-pentyl bromide, and other long-chain aliphatic alkyl halides containing carbon chain length up to 20 carbons.

10. The process as claimed in claim 3, wherein the purification of compound of formula I is carried out using saphadex.

11. A pharmaceutical composition comprising an effective amount of the compound of claim 1 to inhibit proliferation of T-cells or production of cytokine, along with pharmaceutically acceptable excipients and diluents or combination thereof.

12. The composition as claimed in claim 11, wherein the ratio of compound is ranging between 1:99 to 50:50.

13. The composition as claimed in claim 11, wherein the pharmaceutically acceptable excipient is selected from a group consisting of saccharides, lactose, starch, dextrose, stearates, stearic acid, magnesium stearate, polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates, sodium carbonate, sodium bicarbonate, and talc.

14. A method for inhibiting proliferation of T-cells or production of cytokine comprising administering to a patient a therapeutically-effective amount of a compound represented by the formula I:

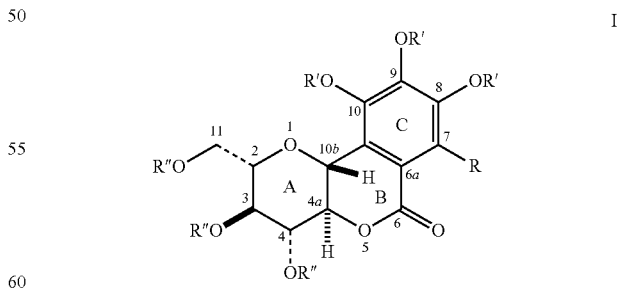

wherein
R is selected from the group consisting of:
—NH-alkyl, —N-dialkyl, —NH-cycloalkyl, substituted or unsubstituted N-cycloalkyl, an alkyl substituted amino group derived from an amino acid, an alkyl substituted amino group derived from a heterocycle, an alkyl substituted amino group derived from N-dialkyl, an alkyl substituted amino group derived from piperidine, an alkyl substituted amino group derived from morpholine, $(C_1-C_6)$-alkyl, $(C_1-C_4)$-haloalkyl, $(C_1-C_4)$-alkoxy, $(C_1-C_4)$-haloalkoxy, $(C_5-C_8)$-cycloalkyl, $(C_5-C_8)$-cycloalkenyl, $(C_6-C_{10})$-bicycloalkyl and $(C_6-C_{10})$-bicycloalkenyl; and R' and R" are each independently selected from the group consisting of hydrogen,
a straight or branched $C_1-C_{10}$ carbon chain, and a branched radical having up to 6 carbon atoms.

15. The method as claimed in claim 14, wherein said patient is a human.

16. The method as claimed in claim 14, wherein the proliferation of T-cells or production of cytokine are associated with an inflammatory disease selected from the group consisting of rheumatoid arthritis, inflammatory bowel disease, psoriasis, asthma and chronic obstructive pulmonary disorder.

17. The process as claimed in claim 4, wherein the amino compound is selected from a group consisting of proline, prolinol, 4-hydroxy proline, morpholine, piperidine, N-methyl piperazine, diethylamine, di-isopropylamine and pyrrolidine.

18. The process as claimed in claim 5, wherein the alkyl halide is selected from the group consisting of methyl iodide, ethyl bromide, propyl bromide, n-butyl bromide, isobutyl bromide, isovaleryl chloride, n-pentyl bromide, and other long-chain aliphatic alkyl halides containing carbon chain length up to 20 carbons.

* * * * *